US012599349B2

(12) United States Patent
Lazarev et al.

(10) Patent No.: US 12,599,349 B2
(45) Date of Patent: Apr. 14, 2026

(54) DETERMINING A THERAPY EFFICACY

(71) Applicant: Arion Diagnostics, Inc., Petaluma, CA (US)

(72) Inventors: Alexander P. Lazarev, Lake Forest, CA (US); Delvin Tai Wai Yuk, Atherton, CA (US); Pavel Lazarev, Box Elder, SD (US)

(73) Assignee: Arion Diagnostics, Inc., Petaluma, CA (US)

( * ) Notice: Subject to any disclaimer, the term of this patent is extended or adjusted under 35 U.S.C. 154(b) by 347 days.

(21) Appl. No.: 18/298,218

(22) Filed: Apr. 10, 2023

(65) Prior Publication Data

US 2023/0270396 A1 Aug. 31, 2023

Related U.S. Application Data

(63) Continuation-in-part of application No. 17/448,888, filed on Sep. 26, 2021, now Pat. No. 11,751,828.

(Continued)

(51) Int. Cl.
*A61B 6/00* (2024.01)
*A61B 5/00* (2006.01)
(Continued)

(52) U.S. Cl.
CPC .............. *A61B 6/502* (2013.01); *A61B 6/467* (2013.01); *A61B 6/563* (2013.01); *G06T 7/0012* (2013.01);
(Continued)

(58) Field of Classification Search
CPC ........... A61P 35/00; A61P 37/04; A61P 11/00; A61P 25/00; A61P 1/04; A61P 43/00;
(Continued)

(56) References Cited

U.S. PATENT DOCUMENTS

| | | | |
|---|---|---|---|
| 5,479,927 A | 1/1996 | Shmulewitz | |
| 5,717,733 A | 2/1998 | Kurbatov et al. | |

(Continued)

FOREIGN PATENT DOCUMENTS

| | | | |
|---|---|---|---|
| CN | 107106998 A | 8/2017 | |
| CN | 112951416 A | 6/2021 | |

(Continued)

OTHER PUBLICATIONS

Arboleda et al, Assessing lesion malignancy by scanning small-angle X-ray scattering of breast tissue with microcalcifications, Phys Med Biol. Aug. 7, 2019;64(15):155010, pp. 1-9.

(Continued)

*Primary Examiner* — Jon Eric C Morales
(74) *Attorney, Agent, or Firm* — MLO, a professional corp.

(57) ABSTRACT

The present disclosure relates to determining an efficacy of a therapeutic agent. A method for determining an efficacy of a therapeutic agent for a target disease can include measuring a molecular structure of a biological tissue of an animal at a first time and at a second time using a non-invasive biological tissue characterization technique. The method can further include observing a change of the molecular structure of the biological tissue between the first time and the second time, and determining the efficacy of the therapeutic agent based on the observed change in the molecular structure of the biological tissue. Before the first time, or between the first time and the second time, the animal received the therapeutic agent.

27 Claims, 4 Drawing Sheets

Related U.S. Application Data which is a continuation of application No. 17/593, 846, filed as application No. PCT/US2021/037224 on Jun. 14, 2021, now Pat. No. 11,607,188.

(60) Provisional application No. 63/039,345, filed on Jun. 15, 2020.

(51) Int. Cl.

| | |
|---|---|
| *A61B 6/46* | (2024.01) |
| *A61B 6/50* | (2024.01) |
| *G06T 7/00* | (2017.01) |
| *G16H 20/10* | (2018.01) |
| *G16H 20/40* | (2018.01) |
| *G16H 30/20* | (2018.01) |
| *G16H 40/63* | (2018.01) |
| *G16H 40/67* | (2018.01) |
| *G16H 50/20* | (2018.01) |

(52) U.S. Cl.

CPC ............. *G16H 20/40* (2018.01); *G16H 30/20* (2018.01); *G16H 40/63* (2018.01); *G16H 40/67* (2018.01); *G16H 50/20* (2018.01); *G06T 2207/10116* (2013.01); *G06T 2207/30068* (2013.01)

(58) Field of Classification Search

CPC .......... A61P 29/00; A61P 19/02; A61P 17/02; A61P 13/02; A61P 13/08; A61P 13/10; A61P 13/12; A61P 15/00; A61P 17/00; A61P 27/02; A61P 3/00; A61P 3/06; A61P 3/08; A61P 3/10; A61P 31/00; A61P 31/04; A61P 31/12; A61P 31/18; A61P 35/02; A61P 37/02; A61P 37/06; A61P 7/00; A61P 7/04; A61P 9/00; A61P 25/02; A61P 25/04; A61P 25/16; A61P 25/28; A61P 35/04; A61N 1/37; A61N 5/10; A61N 1/3629; A61B 5/0071; A61B 5/0075; A61B 5/4839; A61B 6/502; A61B 5/4848; A61B 5/7257; A61B 5/7275; A61B 5/7282

See application file for complete search history.

(56) References Cited

U.S. PATENT DOCUMENTS

| | | | | |
|---|---|---|---|---|
| 5,849,595 | A * | 12/1998 | Alfano .................. | A61B 1/043 422/82.07 |
| 6,175,117 | B1 | 1/2001 | Komardin et al. | |
| 6,483,891 | B1 | 11/2002 | Lazarev et al. | |
| 9,529,974 | B2 | 12/2016 | Li et al. | |
| 11,522,703 | B1 | 12/2022 | Jain et al. | |
| 2003/0014418 | A1 | 1/2003 | Adler et al. | |
| 2003/0135096 | A1 | 7/2003 | Dodds | |
| 2004/0258202 | A1 | 12/2004 | Wernick et al. | |
| 2006/0015265 | A1 | 1/2006 | Raich | |
| 2007/0032832 | A1 | 2/2007 | Feher | |
| 2008/0147554 | A1 | 6/2008 | Stevens et al. | |
| 2013/0208966 | A1 | 8/2013 | Zhao et al. | |
| 2015/0269323 | A1 | 9/2015 | Ginsburg | |
| 2015/0369759 | A1 | 12/2015 | Mazor et al. | |
| 2016/0203263 | A1 | 7/2016 | Maier et al. | |
| 2016/0235372 | A1 | 8/2016 | Schneider et al. | |
| 2017/0362585 | A1 | 12/2017 | Wang et al. | |
| 2018/0038845 | A1 | 2/2018 | Zimmermann et al. | |
| 2018/0122499 | A1 | 5/2018 | Austin et al. | |
| 2019/0046039 | A1 | 2/2019 | Ramesh et al. | |
| 2019/0113451 | A1 | 4/2019 | Weissleder et al. | |
| 2019/0271044 | A1 | 9/2019 | Stephan et al. | |
| 2020/0098476 | A1 | 3/2020 | Loscutoff et al. | |
| 2020/0160980 | A1 | 5/2020 | Lyman et al. | |
| 2020/0242760 | A1 | 7/2020 | Holmes | |
| 2022/0008027 | A1 | 1/2022 | Lazarev et al. | |
| 2022/0013227 | A1 | 1/2022 | Lazarev et al. | |
| 2022/0013233 | A1 | 1/2022 | Lazarev et al. | |
| 2022/0399126 | A1 | 12/2022 | John et al. | |
| 2022/0415505 | A1 | 12/2022 | Lazarev et al. | |
| 2023/0113064 | A1 | 4/2023 | Yuk et al. | |
| 2023/0240635 | A1 * | 8/2023 | Lazarev ................. | A61B 6/502 |
| 2023/0270396 | A1 | 8/2023 | Lazarev et al. | |
| 2023/0341340 | A1 | 10/2023 | Lazarev et al. | |
| 2024/0000412 | A1 | 1/2024 | Lazarev et al. | |
| 2024/0016462 | A1 | 1/2024 | Lazarev et al. | |
| 2024/0161893 | A1 * | 5/2024 | Lazarev .............. | A61B 5/0075 |
| 2025/0149170 | A1 | 5/2025 | Lazarev et al. | |

FOREIGN PATENT DOCUMENTS

| | | | |
|---|---|---|---|
| CN | 113012823 | A | 6/2021 |
| CN | 113533399 | A | 10/2021 |
| CN | 114599407 | A | 6/2022 |
| JP | H0933700 | A | 2/1997 |
| KR | 20180076702 | A | 7/2018 |
| WO | 2004071295 | A1 | 8/2004 |
| WO | 2005112752 | A1 | 12/2005 |
| WO | 2012048000 | A2 | 4/2012 |
| WO | 2013131156 | A1 | 9/2013 |
| WO | 2018081884 | A1 | 5/2018 |
| WO | 2021257451 | A1 | 12/2021 |
| WO | 2021257457 | A1 | 12/2021 |

OTHER PUBLICATIONS

Chapman et al., Diffraction enhanced x-ray imaging, Phys. Med. Biol. 42, Nov. 1997, pp. 2015-2025.

Conceicao et al, Analysis of breast cancer by small angle X-ray scattering (SAXS), Analyst, Apr. 2009 134 (6):1077-82.

Frolov et al., "Risk stratification personalised model for prediction of life-threatening ventricular tachyarrhythmias in patients with chronic heart failure," Kardiologia Polska Mar. 2017; 75, 7: 682-688; DOI: 10.5603/KP.a2017.0060.

James, "Fiber diffraction of skin and nails provides an accurate diagnosis of malignancies", Int. J. Cancer: 125, Feb. 2009, pp. 133-138.

Lazarev et al., "Human Tissue X-ray Diffraction: Breast, Brain, and Prostate", Proceedings of the 22nd Annual International Conference of the IEEE Engineering in Medicine and Biology Society, Cat. No. 00CH37143, vol. 4, Jul. 2000, pp. 3230-3233.

Moss et al., Correlation of X-ray diffraction signatures of breast tissue and their histopathological classification, Scientific Reports, Oct. 2017, pp. 1-9.

Notice of Allowance and Fees dated Feb. 6, 2023 for U.S. Appl. No. 17/593,846.

Notice of Allowance and Fees dated Jul. 19, 2023 for U.S. Appl. No. 17/448,888.

Office Action dated Mar. 22, 2023 for U.S. Appl. No. 17/448,888.

Oliver et al., Diffraction enhanced imaging utilizing a laser produced x-ray source, Rev. Sci. Instrum. 93, 093502, Sep. 2022, 7 pages.

Ortin et al., "Automated real-time method for ventricular heartbeat classification," Computer Methods and Programs in Biomedicine 169 (2019) 1-8, Nov. 2018, 8 pages.

Park, Hye Lyun, Authorized Officer, Korean Intellectual Property Office, "International Search Report" in connection with related International Application No. PCT/US2021/037238, dated Oct. 5, 2021, 5 pgs.

Park, Hye Lyun, Authorized Officer, Korean Intellectual Property Office, Written Opinion of the InternationalSearching Authority in connection with related International Application No. PCT/US2021/037238, dated Oct. 5, 2021, 5 pgs.

Rodriguez, Kari, Authorized Officer, Commissioner for Patents, "International Search Report" in connection with related International Application No. PCT/US2021/037224, dated Sep. 29, 2021, 3 pgs.

(56) References Cited

OTHER PUBLICATIONS

Rodriguez, Kari, Authorized Officer, Commissioner for Patents, Written Opinion of the International Searching Authority in connection with related International Application No. PCT/US2021/037224, dated Sep. 29, 2021, 6 pgs.

Round et al., A preliminary study of breast cancer diagnosis using laboratory based small angle x-ray scattering, Phys Med Biol. Sep. 2005, 50(17):4159-68.

Sidhu et al., Mapping structural changes in breast tissue disease using x-ray scattering, Medical Physics 36, May 2009, pp. 3211-3217.

Wang et al., "A High Precision Real-time Premature Ventricular Contraction Assessment Method based on the Complex Feature Set," Journal of Medical Systems (2020) 44:3, published Nov. 2019, 16 pages.

Wu et al., "ECG signal classification with binarized convolutional neural network," Computers in Biology and Medicine 121, 103800, May 2020, 9 pages.

Yoneyama et al., Fast diffraction-enhanced imaging using continuous sample rotation and analyzer crystal scanning, J Synchrotron Radiat, Mar. 2020, pp. 468-471.

Ahmadian et al., "Monitoring of drug resistance towards reducing the toxicity of pharmaceutical compounds: Past, present and future", Journal of Pharmaceutical and Biomedical Analysis, Mar. 19, 2020, 12 pgs.

Alfenaar, et al., "Therapeutic Drug Monitoring in Non Tuberculosis Mycobacteria Infections", Clinical Pharmacokinetics, Mar. 10, 2021, 15 pgs.

Buclin et al., "The Steps to Therapeutic Drug Monitoring: A Structured Approach Illustrated With Imatinib", Frontiers in Pharmacology, vol. 11, Article 177, Mar. 3, 2020, 10 pgs.

Ghiculescu, "Therapeutic drug monitoring: which drugs, why, when and how to do it", Australian Prescriber, vol. 31, No. 2, Apr. 2008, pp. 42-44.

Iacuzzi et al., "Dried Blood Spot Technique Applied in Therapeutic Drug Monitoring of Anticancer Drugs: a Review on Conversion Methods to Correlate Plasma and Dried Blood Spot Concentrations", Pharm Res, Springer, Apr. 12, 2021, 20 pgs.

James, "A Review of Low Angle Fibre Diffraction in the Diagnosis of Disease", British Journal of Medicine & Medical Research, 3(2): 383-397, Feb. 19, 2013.

James, "Fiber diffraction of skin and nails provides an accurate diagnosis of malignancies", Int. J. Cancer: 125, 133-138, 13 pages, Jul. 2009.

Kuwayama et al., "Time-course measurements of drug concentrations in hair and toenails after single administrations of pharmaceutical products", Drug Testing and Analysis, Jun. 24, 2016, 7 pgs, John Wiley & Sons, Ltd.

Lupien et al., "Effects of stress throughout the lifespan on the brain, behaviour and cognition", Focus on Stress, Jun. 2009, 12 pgs, Macmillan Publishers Limited.

Ong et al., "Optical biosensors—Illuminating the path to personalized drug dosing", Biosensors and Bioelectronics, May 13, 2021, 21 pgs.

Ortiz et al, "Biomarkers of disease in human nails: a comprehensive review", Critical Reviews in Clinical Laboratory Sciences, Oct. 7, 2021, 18 pgs, Taylor & Francis Group.

Todd et al., "Survival in dementia and predictors of mortality: a review", International Journal of Geriatric Psychiatry, Mar. 2013, 16pgs, John Wiley & Sons, Ltd.

Visser, "Techniques for Monitoring Drug Efficacy", Vet Clin North Am Exot Anim Pract., 21(2), May 2018, 287-295, 2018, 7pgs.

Wallenburg et al., "Personalised antimicrobial dosing: standing on the shoulders of giants", International Journal of Antimicrobial Agents, Sep. 2020, 18 pgs.

Wiencek, et al., "Rapid Assessment of Drugs of Abuse", Advances in Clinical Chemistry, Dec. 2016, 33 pgs, Elsevier Inc., Nashville, TN.

Zheng et. al., "Recent advances in drug release monitoring", Nanophotonics,8(3), Feb. 2009, pp. 391-413.

Fagundes et al., "Structural characterization of canine mammary tissue by x-ray diffraction", Radiation Physics and Chemistry, vol. 155, pp. 22-25. (Year: 2019).

Ghammraoui et al., "Maximum-likelihood estimation of scatter components algorithm for x-ray coherent scatter computed tomography of the breast", Physics in Medicine & Biology, vol. 61, pp. 3164-3179. (Year: 2016).

Graewet et al., "Impact and progress in small and wide angle X-ray scattering (SAXS and WAXS)", Current Opinion in Structural Biology, vol. 23, pp. 748-754. (Year: 2013).

Office Action dated Feb. 26, 2024 for U.S. Appl. No. 17/448,886.

Notice of Allowance and Fees dated May 20, 2024 for U.S. Appl. No. 17/448,886.

European Search Report dated May 24, 2024 for European Patent Office Patent Application No. 21826535.3.

European Search Report dated Dec. 4, 2024 for United Kingdom Patent Application No. 2410187.5.

European Search Report dated Dec. 5, 2024 for United Kingdom Patent Application No. 2410185.9.

International Search Report and Written Opinion dated Jan. 17, 2025 for PCT Patent Application No. PCT/IB2024/059571.

International Search Report and Written Opinion dated Jan. 23, 2025 for PCT Patent Application No. PCT/IB2024/060284.

International Search Report and Written Opinion dated Jan. 23, 2025 for PCT Patent Application No. PCT/IB2024/060286.

International Search Report and Written Opinion dated Jan. 31, 2025 for PCT Patent Application No. PCT/IB2024/060287.

Office Action dated Jul. 25, 2025 for U.S. Appl. No. 18/352,085.

Office Action dated Jul. 25, 2025 for U.S. Appl. No. 18/352,094.

Office Action dated Apr. 8, 2025 for U.S. Appl. No. 18/500,624.

Office Action dated Jun. 16, 2025 for U.S. Appl. No. 18/298,190.

Office Action dated Jun. 3, 2025 for U.S. Appl. No. 18/500,604.

Notice of Allowance and Fees dated Oct. 21, 2025 for U.S. Appl. No. 18/298,228.

Office Action dated Oct. 30, 2025 for U.S. Appl. No. 18/352,085.

Choi Mina et al: "Feasibility of imaging amyloid in the brain using small-angle x-ray scattering", Biomedical Physics & Engineering Express, vol. 7, No. 1,Nov. 27, 2020 (Nov. 27, 2020), p. 015008, XP093329220, GB ISSN: 2057-1976, DOI:10.1088/2057-1976/ab501c abstract section "2. Methods".

International Search Report and Written Opinion dated Nov. 7, 2025 for PCT Patent Application No. PCT/IB2025/056737.

Miah et al. ("On-cloud healthcare clinic: an e-health consultancy approach for remote communities in a developing country." Telematics and Informatics 34.1 (2017): 311-322 (Year: 2017).

Notice of Allowance and Fees dated Dec. 2, 2025 for U.S. Appl. No. 18/352,094.

Office Action dated Dec. 8, 2025 for U.S. Appl. No. 18/500,604.

Office Action dated Nov. 26, 2025 for U.S. Appl. No. 18/500,616.

* cited by examiner

100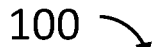

110

Measuring a molecular structure of a biological tissue of an animal at a first time and at a second time using a non-invasive biological tissue characterization technique

120

Observing a change of the molecular structure of the biological tissue of the animal between the first time and the second time, wherein before the first time or between the first time and the second time the animal received a therapeutic agent

130

Determining an efficacy of the therapeutic agent, based on the observed changes of the molecular structure of the biological tissue of the animal between the first time and the second time

FIG. 1

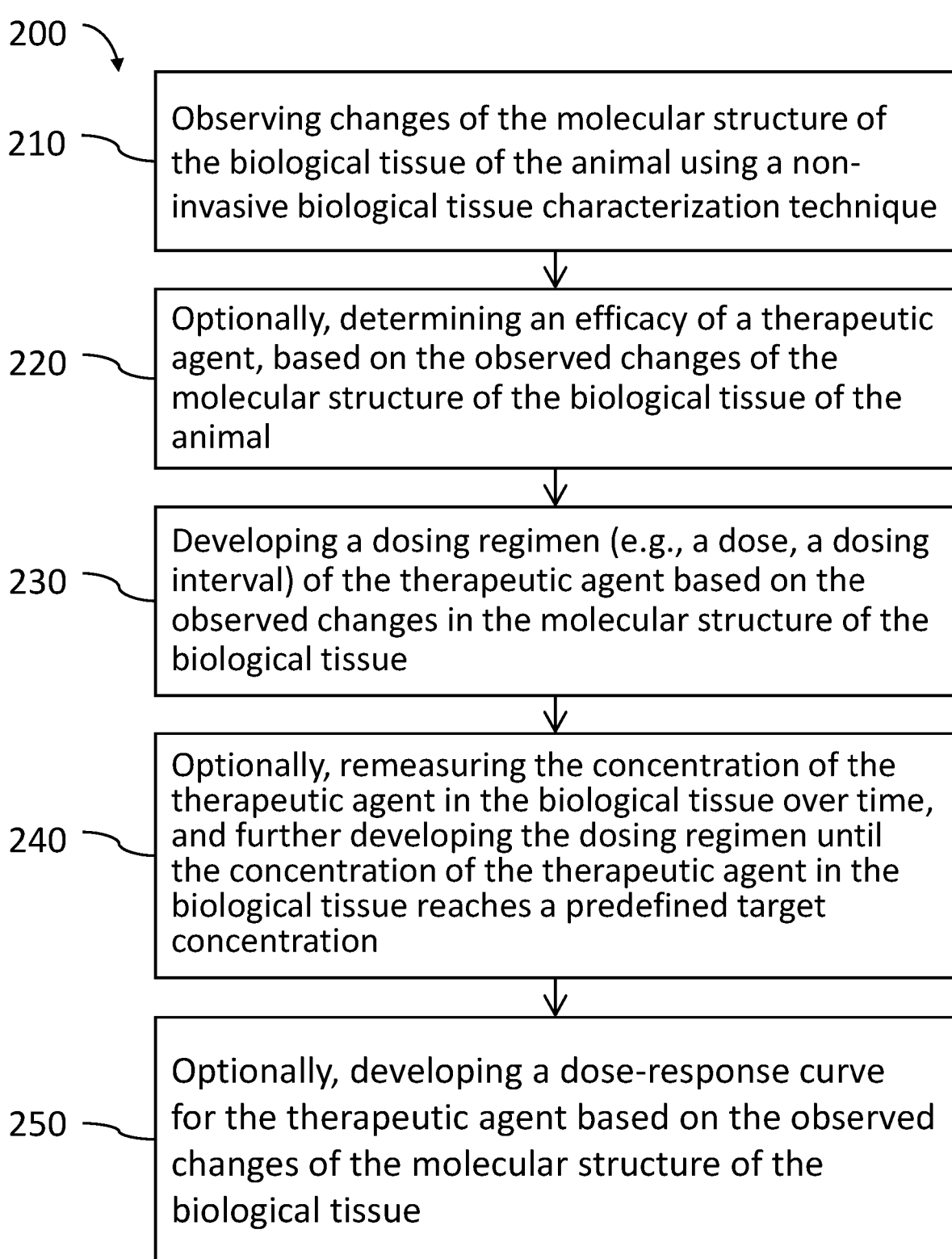

200

210    Observing changes of the molecular structure of the biological tissue of the animal using a non-invasive biological tissue characterization technique 220    Optionally, determining an efficacy of a therapeutic agent, based on the observed changes of the molecular structure of the biological tissue of the animal 230    Developing a dosing regimen (e.g., a dose, a dosing interval) of the therapeutic agent based on the observed changes in the molecular structure of the biological tissue 240    Optionally, remeasuring the concentration of the therapeutic agent in the biological tissue over time, and further developing the dosing regimen until the concentration of the therapeutic agent in the biological tissue reaches a predefined target concentration 250    Optionally, developing a dose-response curve for the therapeutic agent based on the observed changes of the molecular structure of the biological tissue

FIG. 2

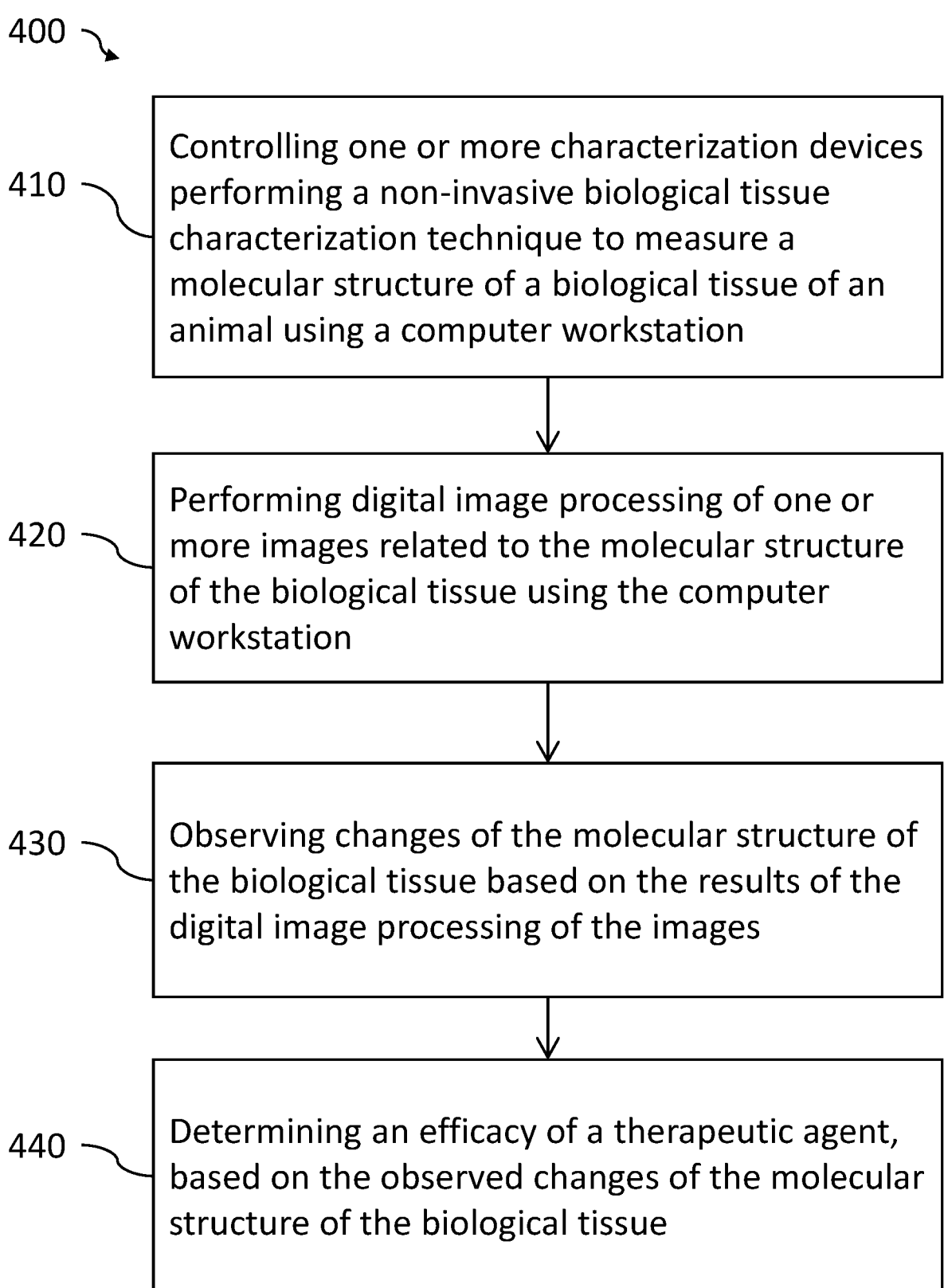

400

410  Controlling one or more characterization devices performing a non-invasive biological tissue characterization technique to measure a molecular structure of a biological tissue of an animal using a computer workstation 420  Performing digital image processing of one or more images related to the molecular structure of the biological tissue using the computer workstation 430  Observing changes of the molecular structure of the biological tissue based on the results of the digital image processing of the images 440  Determining an efficacy of a therapeutic agent, based on the observed changes of the molecular structure of the biological tissue

FIG. 4

DETERMINING A THERAPY EFFICACY

RELATED APPLICATIONS

This application is a continuation-in-part of U.S. patent application Ser. No. 17/448,888, filed Sep. 26, 2021, and entitled "Diffractometer-Based Global In Situ Diagnostic System"; which is a continuation of U.S. patent application Ser. No. 17/593,846, filed Sep. 26, 2021, and entitled "Diffractometer-Based Global In Situ Diagnostic System"; which is a 371 U.S. national phase application of International Application No. PCT/US2021/037224, filed on Jun. 14, 2021, and entitled "Diffractometer-Based Global In Situ Diagnostic System"; which claims priority to U.S. Provisional Patent Application No. 63/039,345, filed on Jun. 15, 2020, and entitled "Diffractometer-Based Global In Situ Diagnostic System"; which are hereby incorporated by reference for all purposes.

BACKGROUND

Determining the efficacy of therapeutic agents used to treat diseases can be challenging due to the limited pharmacokinetic (PK) and/or pharmacodynamic (PD) information available to physicians and veterinarians. Furthermore, identifying criteria for determining the efficacy of different kinds of therapies, such as those with different treatment protocols, purposes of a therapeutic agent used, dose selections, and/or dosing intervals, can also be challenging using conventional methods. Therapy efficacy can furthermore be influenced by a pharmaceutical formulation of a therapeutic agent used in the therapy. For example, clinically relevant differences have been reported in some compounded medications compared with corresponding approved formulations.

Non-invasive biological tissue characterization techniques, for example low angle fiber X-ray diffraction techniques, have been used to measure tissue samples in humans to identify different types of cancer. Fiber diffraction patterns of skin or fingernails, using X-ray sources, have been used as a biometric diagnostic method. The results obtained produce characteristic diffraction patterns which are distinctive and reproducible for a number of cancers including breast cancer, prostate cancer, colon cancer and melanoma.

Therapeutic drug monitoring (TDM) of concentrations of drugs in body fluids, usually plasma, has been done to determine or enhance drug efficacy, reduce toxicity or assist with diagnosis. For example, multi-functional drug delivery systems constructed by a variety of building blocks (e.g., organic molecules, polymeric nanoparticles, micelles, and inorganic nanoparticles), have been developed for drug release monitoring. Non-invasive imaging techniques for monitoring drug release and drug efficacy have also been used in some cases, for example using techniques such as fluorescence imaging, magnetic resonance imaging (MRI), surface-enhanced Raman scattering (SERS), and multi-mode imaging. In some cases, these techniques can further involve using a variety of nanomaterials, such as organic or inorganic nanoparticles, as imaging agents.

SUMMARY

The present disclosure relates to determining an efficacy of a therapeutic agent. In some embodiments, a method for determining an efficacy of a therapeutic agent for treating a disease includes: measuring a molecular structure of a biological tissue of an animal at a first time and at a second time using a non-invasive biological tissue characterization technique; observing a change of the molecular structure of the biological tissue between the first time and the second time; and determining the efficacy of the therapeutic agent based on the observed change in the molecular structure of the biological tissue, wherein before the first time or between the first time and the second time the animal received the therapeutic agent.

BRIEF DESCRIPTION OF THE DRAWINGS

FIG. 1 is a flowchart of an example of a method for determining an efficacy of a therapeutic agent for a disease in an animal, in accordance with some embodiments.

FIG. 2 is a flowchart of an example of a method for determining an efficacy of a therapeutic agent for a disease in an animal, in accordance with some embodiments.

FIG. 4 is a flowchart of an example of a method for determining an efficacy of a therapeutic agent for a disease in an animal, in accordance with some embodiments.

DEFINITIONS

Figure 3A:
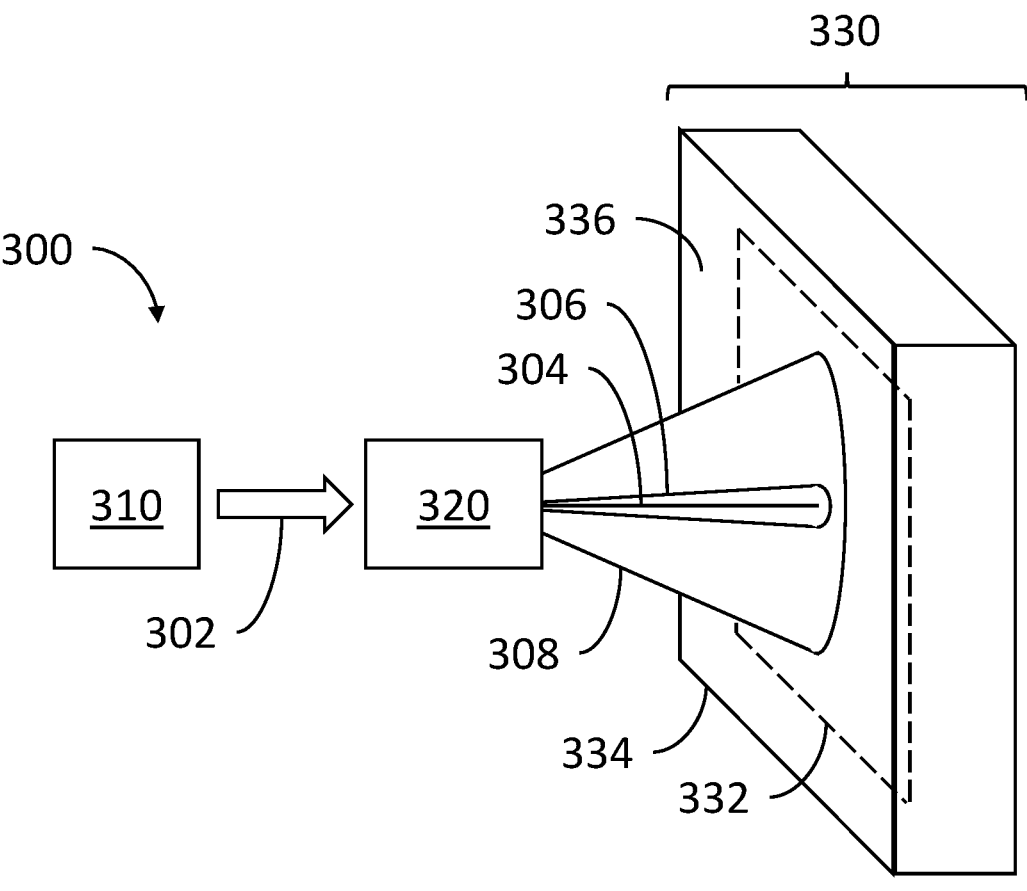
FIGS. 3A and 3B show examples of X-ray tissue diffractometers, in accordance with some embodiments.

As used herein, the term "efficacy" generally refers to the capacity to produce an effect (e.g, lower blood pressure, or change the molecular structure of a biological tissue from a structure indicative of a diseased state to a structure indicative of a healthy state). Efficacy can conventionally be assessed accurately in some situations, such as when patients are selected by proper criteria and strictly adhere to the dosing schedule. For example, conventionally, efficacy can be measured under expert supervision in a group of patients most likely to have a response to a drug, such as in a controlled clinical trial. The patients described herein can be human patients or animal patients.

As used herein, the term "precision medicine" generally refers to a medical model that proposes the customization of healthcare, with medical decisions, treatments, practices, or products being tailored to a subgroup of patients, instead of a one-drug-fits-all model. In precision medicine, diagnostic testing is often employed for selecting appropriate and optimal therapies based on the context of a patient's genetic content or other molecular or cellular analysis.

As used herein, the term "metabolism" generally refers to any chemical process occurring within or between cells. There are two types of metabolism: anabolism, where smaller molecules are synthesized to make larger ones; and catabolism, where larger molecules are broken down into smaller ones. Metabolism is an umbrella term referring to any cellular process that involves a chemical reaction. Glycolysis is an example of a catabolic cellular process; in this process, glucose is broken down into pyruvate.

As used herein, the term "enzyme" generally refers to catalyst which is required to start most chemical reactions within cells. Enzymes, which are large protein molecules found in the body, can be excellent catalysts because they can change the chemicals within the cells without changing themselves.

As used herein, the term "polymorphisms" generally refers to different forms of a DNA sequence. "Poly" means many, and "morph" means form. Polymorphisms are a type of genetic diversity within a population's gene pool. They can be used to map (locate) genes such as those causing a disease, and they can help match two samples of DNA to determine if they come from the same source. Depending on its exact nature, a polymorphism may or may not affect biological function. For example, polymorphism of metabolic enzyme genes may be related with risk of prostate cancer.

As used herein, the term "gut microbiota" generally refers to microorganisms including bacteria and archaea, that live in the digestive tracts of vertebrates including humans, and of insects. The gastrointestinal metagenome (sometimes defined as the microbiome) is the aggregate of all the genomes of gut microbiota. In a human, the gut is the main location of microbiota. The gut microbiota has broad impacts, including effects on colonization, resistance to pathogens, maintaining the intestinal epithelium, metabolizing dietary and pharmaceutical compounds, controlling immune function, and even behavior through the gut-brain axis.

As used herein, the term "non-invasive observation" or "non-invasive biological tissue characterization" of a patient refers an observation or characterization technique that does not include the introduction of instruments into the body of a patient. For example, non-invasive observation or characterization can exclude blood sampling and the introduction of pathogenic viruses and bacteria into the body. Non-invasive observation or characterization can advantageously spare the patient from pain. In some cases, non-invasive observation or characterization can eliminate radiation exposure to the body.

As used herein, the term "biological tissue" or "biological tissue sample" generally refers to tissue (or tissue samples) of a patient. For example, biological tissue can include materials of living organs that contain structural molecular components and functional components like cells, muscles, and skin, as well as detachable structures like hair, nail, skin, wool, horns, claws, or pelt. In some cases, biological tissue can contain biological molecular structures such as collagens, keratins and glycoproteins that diffract X-ray light.

As used herein, the term "X-ray tissue diffractometer" generally refers to a diffractometer configured to record diffraction data from one or more tissue sites including structural and functional molecular structures, for example sites in cells, skin and hair.

As used herein, the term "cancer" generally refers to a proliferative disorder caused or characterized by a proliferation of cells which have lost susceptibility to normal growth control. Cancers of the same tissue type usually originate in the same tissue and may be divided into different subtypes based on their biological characteristics. In some cases, malignant tumors (cancer) can be further classified according to morphological characteristics, such as: a) epithelial (papillomas, adenomas, carcinomas, cysts, dermatomas); b) connective tissue (fibroids, myxomas, lipomas, chondromas, osteomas, melanosarcomas); c) nervous tissue (gliomas, neurinomas, meningiomas); d) muscle (fibroids, rhabdomyomas); e) vascular (hemangiomas and lymphangiomas); f) mixed (osteosarcomas and fibromyxochondroma, fibrochondroosteoma).

As used herein, the term "the dose-response relationship" or "dose-response curve" generally refers to a dependence between a dose of a therapeutic agent and a response of a subject (e.g., an animal or a human) given the therapeutic agent. Some example responses include measures of effectiveness and/or toxicity of the therapeutic agent. The dose-response relationship (or dose-response curve) illustrates the response (or effect) associated with a given dose of the therapeutic agent.

As used herein, the term "therapeutic window" generally refers to a range of doses of a therapeutic agent that can be used in a therapy. For example, a therapeutic window can take into account a maximum concentration of the therapeutic agent in a tissue sample (Cmax), above which there is an increased risk of developing an adverse event, and a minimum concentration of the therapeutic agent in the tissue sample (Cmin), below which the therapeutic agent is ineffective.

As used herein, the term "pharmacokinetic (PK) data" generally refers to reports including data about how a patient's body (or tissue) responds to a drug, including absorption to metabolism, distribution, and excretion.

As used herein, the term "pharmacodynamic (PD) studies" generally refers to studies that describe how a drug interacts with the body (or tissue) of a patient in a dose dependent manner, for example, including anticipated and unanticipated (adverse) responses.

As used herein, the term "image segmentation" generally refers to a method used in digital image processing and computer vision, including a process of partitioning a digital image into multiple image segments (also known as image regions, image objects, or sets of pixels). The goal of segmentation can be to simplify and/or change the representation of an image into something that is more meaningful and easier to analyze. Image segmentation is typically used to locate objects and boundaries (e.g., lines, curves, etc.) in images. Additionally, image segmentation can include the process of assigning a label to every pixel in an image such that pixels with the same label share certain characteristics.

As used herein, the term "recognition of objects" or "object recognition" generally refers to a field of computer vision wherein objects are found and/or identified in an image (or one or more images from a video sequence).

As used herein, the term "target disease" generally refers to a disease that is intended to be treated by a therapeutic agent being tested. Some examples of target diseases are melanoma, breast, colon, and prostate cancers and Alzheimer's disease. Other examples of target diseases include diseases of the immune system, rheumatic diseases, cancer, or diseases of one or more of the: skin, stomach, liver, rectum, colon, esophagus, pancreas, bladder, vagina, lung, oropharynx, nasopharynx, oral mucosa, tongue, brain, thyroid, prostate, breast, cervix, ovary, urological organs, endocrine organs, veins, lymph nodes, mammary glands, respiratory organs, digestive organs, heart, blood vessels, colon, ear, throat, or nose.

As used herein, the term "animal" generally refers to a non-human living organism. Some examples of animals are non-human mammals such as dogs, cats, rats, mice, rabbits, guinea pigs, hamsters, and monkeys, and non-mammals such as birds, reptiles and amphibians.

As used herein, the term "laboratory animals" generally refers to animals that are bred for laboratory experiments. Some examples of laboratory animals are rabbits, guinea pigs, white rats, gray rats, white mice, gray mice, and golden hamsters. Laboratory animals can be bred to study various biological systems, such as the nervous system, metabolism and digestion, reproduction, hormones, and the immune system, as well as various conditions, such as cancer, cardiovascular diseases, and mental health disorders. Laboratory animals can also be bred to determine an efficacy of a therapeutic agent for treating a target disease.

DETAILED DESCRIPTION

The present disclosure provides a method for determining an efficacy of a therapeutic agent (e.g., a drug or biologic)

for treating a target disease including observing changes in a molecular structure of biological tissue samples over time. In some cases, the biological tissue can be collagens, keratins, or glycoproteins that diffract X-rays. In some cases, the measured data can be analyzed using digital image processing, for example including pattern recognition and the recognition of objects in X-ray diffraction images.

X-ray diffraction systems and methods for characterizing biological tissue samples are further described in U.S. patent application Ser. Nos. 17/593,846 and 17/448,888, which are hereby incorporated by reference in their entireties.

Laboratory animals can be used to study the efficacy of therapeutic agents, such as anticancer drugs, biologics, antiretrovirals, antiinfectives, and psychotropic agents. "Biologics" can include any agent(s) manufactured in a living system (e.g., in a microorganism, or a plant or animal cell using recombinant DNA technology). In some cases, biologics are large complex molecules, or mixtures of molecules. In some cases, a laboratory animal is infected with a target disease, and then given a therapy for the target disease including the administration of a therapeutic agent. The efficacy of the therapeutic agent can be determined using measurements of a molecular structure of a biological tissue of the animal over time. In some cases, a dosing regimen, a dose and dosing interval, a median effective dose (ED50), and/or a therapeutic window can be developed based on the measurements of the molecular structure of the biological tissue of the animal over time. A median effective dose (ED50) is a dose at which at least 50% of a population of laboratory animals receiving the therapeutic agent has a desired response (e.g., a desired change in the molecular structure of the biological tissue of the laboratory animal over time, a desired effectiveness, and/or a lack of toxicity). In some cases, the dosing regimen, dose and dosing interval, ED50, and/or a therapeutic window can be further refined or adjusted based on the measurements of the molecular structure of the biological tissue of the animal over time. In some cases, the developed dosing regimen, dose and dosing interval, ED50, and/or a therapeutic window can be used to develop a dosing regimen, dose and dosing interval, ED50, and/or a therapeutic window for a therapy for human patients with the target disease. Additionally, a therapeutic index (TI) can be calculated from the ED50 and a median lethal dose (LD50), wherein TI is the LD50 divided by the ED50. A median lethal dose (LD50) is a dose at which at least 50% of a population of laboratory animals receiving the therapeutic agent has a lethal response.

Systems and methods to monitor therapeutic agents for in vitro and in vivo use can advantageously: accurately locate diseased tissues, avoid inappropriate therapeutic agent dosage, and/or improve therapeutic efficiency. The present disclosure describes systems and methods to monitor therapeutic agents and the efficacy thereof, for example, including real-time monitoring of therapeutic agent release inside targeted cells or in living animals or humans.

Conventional therapeutic drug monitoring (TDM) includes measuring concentrations of drugs in bodily fluids (e.g., blood and plasma) and has been done to enhance drug efficacy, reduce toxicity or assist with diagnosis. Despite the apparent advantages of TDM, it has inherent limitations. For example, conventional drug assays are costly, and require invasive sampling of blood. Additionally, blood samples are conventionally analyzed using expensive chromatographic or immunoassay-based machines, at times in centralized laboratories. These techniques typically result in long turnaround times, high instrumentation costs and intensive skilled labor requirements. Therefore, the reason for performing conventional TDM and the additional information to be gained (if any) is generally carefully considered against the costs. Conventional TDM also has limited uses, for example, because the monitored concentrations of some drugs have not been clearly related to their effects. Due to the importance of early detection of therapeutic agent efficacy (e.g., in patients with infectious diseases or cancers), reliable and accurate TDM methods with fast turnaround times are needed.

The methods to monitor therapeutic agents described herein can include the following: 1) developing a dose-response curve, for example including a combination of pharmacokinetic (PK) and pharmacodynamic (PD) data, to determine a therapeutic agent efficacy; 2) monitoring for adverse events, including any reported toxicities, to determine therapeutic agent efficacy; 3) monitoring clinical response, imaging, and diagnostics such as complete blood count, biochemistry, and urinalysis, to determine therapeutic agent efficacy; and/or 4) determining plasma therapeutic agent concentration in a patient, and tailor a dose of the therapeutic agent based on clinical signs or adverse therapeutic agent events.

FIG. 1 is a flowchart of an example of a method 100 for determining an efficacy of a therapeutic agent for treating a target disease including the following blocks. In block 110, a molecular structure of a biological tissue of an animal is measured at a first time and at a second time using a non-invasive biological tissue characterization technique. At block 120, a change of the molecular structure of the biological tissue is observed (or determined, or calculated) between the first time and the second time, such as by analyzing data from the measurements from non-invasive biological tissue characterization technique at the first time and the second time using a computer processor. In block 130, the efficacy of the therapeutic agent is determined based on the observed change in the molecular structure of the biological tissue. In some cases, an observed change in the molecular structure of a biological tissue can be that no change (or no significant change) occurred in the molecular structure of a biological tissue. In this case, the animal received the therapeutic agent either before the first time, or between the first time and the second time, thereby allowing the observed change in the molecular structure of the biological tissue to provide feedback regarding the efficacy of the therapeutic agent. In some cases, method 100 further includes infecting the animal with the target disease, either before the first time, or between the first time and the second time.

Therapies for diseases such as cancer (e.g., melanoma, breast, colon, and prostate cancers) and Alzheimer's disease can change structural properties (e.g., an alignment of molecules) of a biological tissue, which can be monitored using characterization techniques (e.g., X-ray diffraction), and the efficacy of therapeutic agents used in such therapies can be determined using the methods described herein (e.g., method 100). Therapeutic agents for treating other diseases, the efficacy of which can be evaluated using the current methods, include therapeutic agents for treating diseases of the immune system, diseases of the skin, oncological disease, rheumatic diseases, urological diseases, endocrine diseases, diseases of veins and lymph nodes, diseases of the mammary glands, diseases of respiratory organs, diseases of digestive organs, diseases of heart and blood vessels, diseases of the colon, diseases of the ear, diseases of the throat, and diseases of the nose. For example, an oncological disease can include cancer of the stomach, liver, rectum and colon, esophagus, pancreas, bladder, vagina, lung, oropharynx, nasopharynx, oral mucosa, tongue, skin, brain, thyroid, prostate, breast, cervix, and/or ovary. Therapeutic agent efficacy (e.g., the efficacy of an administered drug or biologic) can be determined by characterizing the changes in the structural properties of a biological tissue of an animal (e.g., a sample of biological tissue taken from the animal measured ex vivo, or a biological tissue of the animal measured in vivo) over the course of treatment. In some cases, changes of a structure of an extracellular matrix on an organism level in response to morphogenesis in organs allows monitoring of the changes in the extracellular matrix in sites remote from site of morphogenesis. For example, a molecular structure of a biological tissue that is remote from a site of a disease, such as hair, nail, skin, wool, horns, claws, or pelt, can be measured to determine the efficacy of a therapeutic agent used for treating for the disease. In some cases, an effective therapeutic agent that causes diseased tissue to become healthy (or be eliminated) can be confirmed by directly monitoring improvements in the structural properties of the biological tissue of the animal (e.g., in measurements taken in the same region of the animal over time, where the tissue in that region may or may not change). Conversely, an ineffective therapeutic agent can be identified by directly observing that diseased tissue remains (e.g., in measurements taken of biological tissue in (or from) the same location of the animal throughout (and after) the course of treatment.

In some embodiments, the methods disclosed herein are precision medicine methods and provide rational dosing regimens adapted to an animal or patients' characteristics that can relevantly benefit patients (animal or human) in clinical practice, for example, by preventing or correcting both under-dosing deleterious to therapeutic efficacy and overdosing leading to toxicity and subsequent treatment cessation.

In some embodiments, method 100 of FIG. 1 further includes adapting a dosing regimen of the therapeutic agent that is used in the therapy to characteristics of the animal, wherein the dosing regimen prevents or corrects both under-dosing deleterious to the efficacy of the therapy and over-dosing leading to toxicity.

In some embodiments, the methods disclosed herein can be used to determine the efficacy of a therapeutic agent including one or more of the following: anticancer drugs, biologics, antiretrovirals, antiinfectives, and psychotropic agents.

In some embodiments, the methods disclosed herein include optimizing the efficacy of the therapeutic agent that is used in a therapy for a specific animal, including taking into account one or more characteristics of: a gender of the animal, a metabolic enzyme polymorphism of the animal, a gut microbiota of the animal, a time of administration of the first therapeutic agent, a presence of hepatic or renal disease in the animal, and an interaction between the first therapeutic agent and a second therapeutic agent used by the animal.

In some embodiments, the methods disclosed herein include measuring (e.g., in block 110 of method 100 in FIG. 1) a molecular structure of biological tissue that diffracts X-ray light, such as a collagen, a keratin, and/or a glycoprotein.

In some embodiments, the biological tissue measured in the methods disclosed herein (e.g., in block 110 of method 100 in FIG. 1) include breast tissue, brain tissue, hair, nail, skin, wool, horns, claws, and/or pelt.

In some embodiments, the non-invasive biological tissue characterization technique of the methods disclosed herein includes one or more of: X-ray diffraction (e.g., using a tissue diffractometer comprising a two-dimensional pixel detector), luminescent spectroscopy, selective laser spectroscopy, Raman spectroscopy, spectroscopy in the visible spectral region (e.g., 400-740 nm), and infrared spectroscopy.

In some embodiments, the methods disclosed herein (e.g., in block 120 of method 100 in FIG. 1) the non-invasive observation of the changes in the molecular structure of the biological tissue samples is implemented by a device such as X-ray tissue diffractometer comprising a two-dimensional pixel detector, luminescent spectroscope, selective laser spectroscope, Raman spectroscope, spectroscope in the visible spectral region (400-740 nm), and infrared spectroscope. In some embodiments, one or more processors (or computers, or servers) are used to process data from the device. In some embodiments, the processed data can further be used by the one or more processors (or computers, or servers) to determine the efficacy of the therapeutic agent (e.g., in block 130 in method 100 in FIG. 1).

In some cases, in block 120 of method 100, the observed change in the molecular structure of the biological tissue can indicate a change in a trajectory. For example, a therapy including administering a therapeutic agent can be started at a first time (i.e., a first point in time, such as a certain date), and cause a first observed change in the molecular structure of the biological tissue, and that can indicate a first efficacy of the therapeutic agent. Subsequently, a second change in the molecular structure of the biological tissue can be observed at a second time (i.e., a second point in time, such as a second date), which indicates a second efficacy of the therapeutic agent (e.g., in a second time period) that is different from the first efficacy. In some cases, the therapeutic agent can be more efficacious in the first observation, and in other cases, the therapeutic agent can be more efficacious in the second observation.

In some embodiments, the methods disclosed herein include measuring concentrations of a therapeutic agent (e.g., a drug) in the biological tissue samples. In some cases, the concentration of the therapeutic agent can be measured until a defined target concentration is reached, for example, associated with optimal efficacy and minimal toxicity. In some cases, the method can include measuring a concentration of a therapeutic agent in the biological tissue sample using an optical technique, such as luminescent spectroscope, selective laser spectroscope, Raman spectroscope, spectroscope in the visible spectral region (400-740 nm), and infrared spectroscope. The measurements of the concentration of the therapeutic agent can improve animal patient care by providing information about the amount of the therapeutic agent in the biological tissue over time, which can be used to determine the efficacy of the therapeutic agent, or determine (or adapt) a dosing regimen of the therapeutic agent. For example, the dosing regimen can be adapted and the concentrations of the therapeutic agent in the biological tissue can be measured until the concentration of the therapeutic agent in the biological tissue reaches a predefined target concentration (e.g., associated with optimal efficacy and minimal toxicity).

In some embodiments, more than two measurements of a molecular structure of a biological tissue of an animal are taken over time in block 110 of method 100. In such cases, in block 120 changes in the molecular structure of the biological tissue can be observed using an algorithm to analyze the change in the molecular structure over time (wherein the change can include no change, or no significant change). For example, the algorithm can analyze the measurement data to determine the change in the molecular structure after each successive measurement. The output from the algorithm indicating the change in molecular structure over time can be used to determine the efficacy of the therapeutic agent, and/or change the therapy (e.g., change the dose or dosing interval of a therapeutic agent, or change to a different therapeutic agent). In cases where a series of measurements are taken, the "first time" in method 100 can correspond to the first measurement in the series of measurements (either before or after starting the therapy), or the "first time" in method 100 can correspond to a measurement other than the first measurement in the series of measurements. Additionally, when a series of measurements are taken, the first time and the second time can be consecutive or non-consecutive measurements.

In block 110 of method 100, measurements of the molecular structure of the biological tissue can be taken at various times following the initiation of, during treatment by, or after completion of a therapy including the administration of a therapeutic agent. The data from the measurements can be analyzed after each successive measurement or at selected intervals using a multi-step algorithm. In some cases, the multi-step algorithm includes statistical analyses to determine the change of the molecular structure of the biological tissue in block 120 (e.g., after each measurement). In some cases, more than one measurement can be taken at a particular time (e.g., on the same day, or in a single measurement session), for example, to provide more data for statistical analyses. In some cases, the statistical analyses can include fitting measured data to a function (e.g., a linear function, a polynomial function, an exponential function, or a logarithmic function) to determine the change of the molecular structure of the biological tissue. In this process, regression coefficients of the fitted functions can be determined using the statistical analyses. In some cases, comparison of regression coefficients of functions that have been fit to the measured data using multiple measurements can improve the statistical significance of an observed change of the molecular structure of the biological tissue over time. In some cases, the statistical analyses may include a determination of a pair-wise distance distribution function, a determination of a Patterson function, a calculation of a Porod invariant, a Fourier transformation, a cluster analysis, a dispersion analysis, a determination of one or more molecular structural periodicities, or any combination thereof. In some cases, the multi-step algorithm can analyze the clustering of data (e.g., derived from the analysis of image data, diffraction data, subject data, or any combination thereof) and re-evaluate observed changes in sample data characteristics and clustering over time. In some cases, the multi-step algorithm can plot patient sample data points in an n-dimensional space defined by two or more parameters of the therapy (e.g., a degree of crystallinity of a molecular structure, time, therapeutic agent dose, etc.) and analyze the data for changes in the molecular structure. For example, the distance or changes in distance between data points or clusters of data points may be calculated as a function of time. In some instances, the proximity of a new data point to the previous data point(s), or the trajectory of certain data clusters (or the gradient of the trajectory) can describe the observed change in the molecular structure of the biological tissue over time. These factors may be used as indicators for the efficacy of the therapeutic agent and/or can be interpreted by a physician in terms of therapeutic agent efficacy. In some instances, the output of the multi-step algorithm can be used to directly monitor the efficacy of a therapeutic agent. Comparing the results of assessments for multiple patients can also provide indications of the efficacy of a therapeutic agent in a patient or in groups of patients.

FIG. 2 is a flowchart of an example method 200 for determining an efficacy of a therapeutic agent for treating a target disease. In block 210, changes of the molecular structure of the biological tissue of the animal are observed using a non-invasive biological tissue characterization technique. The method performed in block 210 can be similar to that performed in block 120 in method 100 in FIG. 1. In optional block 220, an efficacy of a therapeutic agent is determined, based on the observed changes of the molecular structure of the biological tissue of the animal. The method performed in optional block 220 can be similar to that performed in block 130 in method 100 in FIG. 1. In block 230, a dosing regimen (e.g., a dose, a dosing interval) of the therapeutic agent is adapted based on the observed changes in the molecular structure of the biological tissue. In optional block 240, the concentration of the therapeutic agent in the biological tissue is measured (or remeasured) over time, and the dosing regimen is further adapted until the concentration of the therapeutic agent in the biological tissue reaches a predefined target concentration. In optional block 250, a dose-response curve for the therapeutic agent is developed based on the observed changes of the molecular structure of the biological tissue. One or more blocks 210, 220, 230, 240 and 250 of method 200 can be performed wholly or partially by a computer processor (or computer, or server). For example, a computer processor can process data from a characterization technique in block 210 and/or 220.

In some embodiments, the methods disclosed herein include measuring, in the biological tissue, a concentration of a therapeutic agent that is used in a therapy using a non-invasive biological tissue characterization technique. The method can further include adapting a dosing regimen of the therapeutic agent based on the observed changes in the molecular structure of the biological tissue. In some embodiments, the method further includes remeasuring the concentration of the therapeutic agent in the biological tissue over time, and further adapting the dosing regimen (e.g., determining a dosing interval to achieve efficacy or safety) until the concentration of the therapeutic agent in the biological tissue reaches a predefined target concentration (e.g., associated with optimal efficacy and minimal toxicity). In some embodiments, the method further includes developing a therapeutic window for the therapeutic agent, wherein the therapeutic window includes a maximum concentration of the therapeutic agent in the tissue (Cmax), above which there is an increased risk of developing an adverse event, and a minimum concentration of the therapeutic agent in the tissue (Cmin) below which concentrations are ineffective.

In some embodiments, the methods disclosed herein include using a computer workstation to control a characterization device performing the non-invasive biological tissue characterization, such as one or more spectroscopes and/or an X-ray tissue diffractometer. In some cases, the mechanisms and motors of the characterization device, and/or analysis and storage of data from the characterization device (e.g., digital image processing, storing and displaying data received from the two-dimensional pixel detector) can also be performed using the computer workstation. For example, digital image processing can include discrete two-dimensional Fourier transform of images, image segmentation, definition of descriptors of boundaries and regions, and/or recognition of objects within one or more images.

In some embodiments, the methods disclosed herein include controlling one or more characterization devices performing the non-invasive biological tissue characterization technique using a computer workstation. The method can further include digital image processing of one or more images related to the molecular structure of the biological tissue which can also be performed using the computer workstation. For example, the digital image processing can include one or more of: producing a discrete two-dimensional Fourier transform of the one or more images, performing image segmentation of the one or more images, defining descriptors of boundaries or regions in the one or more images, and recognizing objects in the one or more images. The method can further include storing and displaying data received from the characterization device performing the one or more characterization techniques.

Figure 3B:
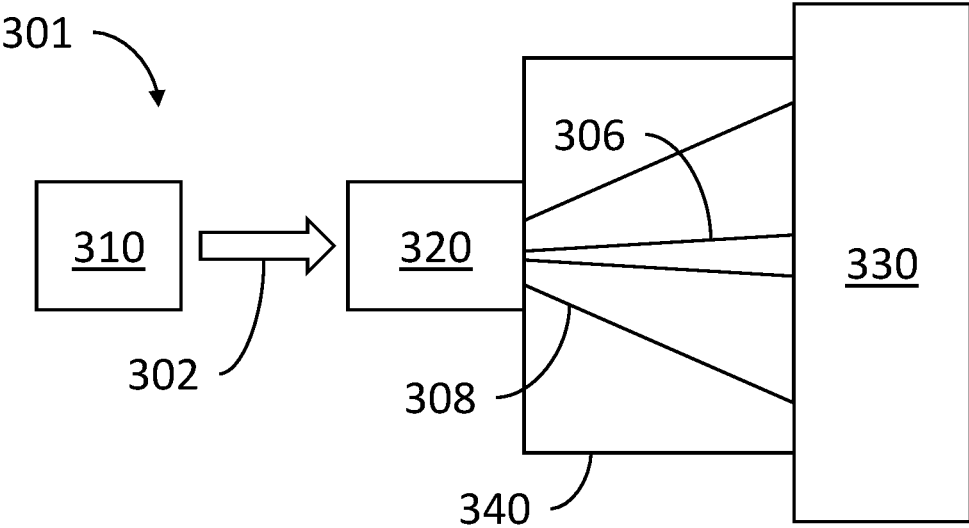

In some embodiments, the non-invasive biological tissue characterization technique of the methods disclosed herein is X-ray diffraction, and the measurements are performed using an X-ray tissue diffractometer. FIGS. 3A and 3B show examples of X-ray tissue diffractometers 300 and 301 that can be used to perform the methods disclosed herein.

FIG. 3A shows a simplified schematic of an example of an X-ray tissue diffractometer 300 including: a positioning area 320 for the biological tissue, an X-ray beam delivery system 310 and a receiver 330. The X-ray beam delivery system 310 provides a primary incident micro-beam of X-rays 302 directed at the biological tissue to be analyzed (the biological tissue being held in positioning area 320). The X-ray beam delivery system 310 can include a radiation source operating in continuous mode, an apparatus forming X-ray micro-beam, at least one monochromator, and at least one collimating and focusing optical device. The receiver 330 can include a two-dimensional pixel detector 332 designed to detect the transmitted micro-beam of X-ray 304 passed through the analyzed biological tissue as well as part or all X-rays 306 and 308 that are diffracted by the biological tissue. X-rays 306 are small-angle x-ray scattering (SAXS) signals, and X-rays 308 are wide-angle x-ray scattering (WAXS) signals, both of which can be detected using receiver 330. In some cases, the two-dimensional pixel detector 332 can be inside a protection container 334 that contains a vacuum (or low pressure) environment or is filled with an inert gas (e.g., neon or helium), and includes a window or wall 336 facing the biological tissue that is substantially transparent to X-rays.

FIG. 3B shows another simplified schematic of an example of an X-ray tissue diffractometer 301, which further comprises a chamber 340 filled with an inert gas (e.g., neon or helium). Chamber 340 is located between the receiver 330 and the positioning area 320 for the biological tissue in a working state (e.g., during the X-ray diffraction characterization of the molecular structure of the biological tissue). In some cases, the chamber 340 can be moveable, and can be moved into a different position in a non-working state. In some cases, receiver 330 can also include two-dimensional pixel detector 332, and chamber 334 with window or wall 336 that is substantially transparent to X-rays.

FIG. 4 is a flowchart of an example method 400 for determining an efficacy of a therapeutic agent for treating a target disease. In block 410, one or more characterization devices performing a non-invasive biological tissue characterization technique are controlled to measure a molecular structure of a biological tissue of an animal using a computer workstation (or computer processor, or computer, or server). In block 420, digital image processing of one or more images related to the molecular structure of the biological tissue are performed using the computer workstation (or computer processor, or computer, or server). In block 430, changes of the molecular structure of the biological tissue are observed, based on the results of the digital image processing of the images. In block 440, an efficacy of a therapy is determined, based on the observed changes of the molecular structure of the biological tissue. Blocks 430 and 440 of method 400 can be performed wholly or partially by a computer workstation (or computer processor, or computer, or server). For example, a computer processor can process data from a characterization technique in block 430 and/or 440.

In some embodiments, the methods disclosed herein include monitoring a clinical response of the animal (e.g., using visualization and diagnostics), such as a general blood test, a biochemical analysis, and/or a urine analysis. In some cases, these clinical responses can provide an indication of the status of the animal using conventional means, which can be used in combination with the methods described herein to further determine the efficacy of a therapeutic agent. In some cases, information from the monitoring the clinical response can be used for comparative analysis and testing of the disclosed method, and can be used to further determine the efficacy of the therapeutic agent (e.g., in combination with using the non-invasive biological tissue characterization technique to observe changes in the molecular structure of the biological tissue).

In some embodiments, the methods disclosed herein include drawing a dose-response curve for a therapeutic agent used in the therapy, using the observed changes of the molecular structure of the biological tissue. The non-invasive biological tissue characterization techniques of the methods described herein can be used to provide information about the response, which can be used to draw the dose-response curve. In some cases, a dose and/or dosing interval can be determined based on a measurement of a concentration of the therapeutic agent in the tissue (e.g., to achieve efficacy or safety). In some cases, a dose and dosing interval of the therapeutic agent is developed based on the observed change of the molecular structure of the biological tissue (e.g., that is effective while minimizing risk of an adverse event). In some embodiments, a therapeutic window for the therapeutic agent can be developed, which includes a maximum concentration of the therapeutic agent in the tissue (Cmax), above which there is an increased risk of developing the adverse event, and a minimum concentration of the therapeutic agent in the tissue (Cmin) below which concentrations are ineffective.

The methods disclosed herein include methods for determining an efficacy of a therapeutic agent used for treating a disease in an animal using non-invasive biological tissue characterization. The present methods are advantageous, since determining the efficacy of therapeutic agent for various diseases in animals can be challenging due to the limited pharmacokinetic (PK) and/or pharmacodynamic (PD) information available. The present methods can advantageously address the issues with conventional techniques, using non-invasive biological tissue characterization to directly determine the efficacy of a therapeutic agent.

Reference has been made to embodiments of the disclosed invention. Each example has been provided by way of explanation of the present technology, not as a limitation of the present technology. In fact, while the specification has been described in detail with respect to specific embodiments of the invention, it will be appreciated that those skilled in the art, upon attaining an understanding of the foregoing, may readily conceive of alterations to, variations of, and equivalents to these embodiments. For instance, features illustrated or described as part of one embodiment may be used with another embodiment to yield a still further embodiment. Thus, it is intended that the present subject matter covers all such modifications and variations within the scope of the appended claims and their equivalents. These and other modifications and variations to the present invention may be practiced by those of ordinary skill in the art, without departing from the scope of the present invention, which is more particularly set forth in the appended claims. Furthermore, those of ordinary skill in the art will appreciate that the foregoing description is by way of example only, and is not intended to limit the invention.

What is claimed is:

1. A method for determining an efficacy of a therapeutic agent for treating a target disease, the method comprising:

measuring a molecular structure of a biological tissue of an animal at a first time and at a second time using a non-invasive biological tissue characterization technique;

observing a change of the molecular structure of the biological tissue between the first time and the second time;

determining the efficacy of the therapeutic agent based on the observed change in the molecular structure of the biological tissue, wherein before the first time or between the first time and the second time the animal received the therapeutic agent, and before the first time or between the first time and the second time, infecting the animal with the target disease.

2. The method of claim 1, wherein the therapeutic agent is selected from:

anticancer drugs, biologics, antiretrovirals, antiinfectives, psychotropic agents.

3. The method of claim 1, further comprising developing a dosing regimen of the therapeutic agent using the observed change of the molecular structure of the biological tissue and using characteristics of the animal, wherein the dosing regimen prevents or corrects both under-dosing deleterious to the efficacy of the therapeutic agent and overdosing leading to toxicity.

4. The method of claim 3, wherein the characteristics of the animal comprise one or more of: a gender of the animal, a metabolic enzyme polymorphism of the animal, a gut microbiota of the animal, a time of administration of the therapeutic agent, a presence of hepatic or renal disease in the animal, and an interaction between the therapeutic agent and a second therapeutic agent administered to the animal.

5. The method of claim 1, wherein the biological tissue is one or more of: a collagen that diffracts x-ray light, a keratin that diffracts x-ray light, and a glycoprotein that diffracts X-ray light.

6. The method of claim 1, wherein the biological tissue comprises one or more of breast tissue, brain tissue, hair, nail, skin, wool, horns, claws, or pelt.

7. The method of claim 1, wherein the non-invasive biological tissue characterization technique comprises one or more of: X-ray diffraction, luminescent spectroscopy, selective laser spectroscopy, Raman spectroscopy, spectroscopy in the visible spectral region, and infrared spectroscopy.

8. The method of claim 7, wherein the method further comprises:

measuring, in the biological tissue, a concentration of the therapeutic agent using the non-invasive biological tissue characterization technique; and developing a dosing regimen of the therapeutic agent based on the observed changes in the molecular structure of the biological tissue.

9. The method of claim 8, further comprising remeasuring the concentration of the therapeutic agent in the biological tissue over time, and further developing the dosing regimen until the concentration of the therapeutic agent in the biological tissue reaches a predefined target concentration.

10. The method of claim 8, further comprising developing a therapeutic window for the therapeutic agent, wherein the therapeutic window includes a maximum concentration of the therapeutic agent in the biological tissue (Cmax), above which there is an increased risk of developing an adverse event, and a minimum concentration of the therapeutic agent in the biological tissue (Cmin) below which concentrations are ineffective.

11. The method of claim 7, further comprising:

controlling one or more characterization devices performing the non-invasive biological tissue characterization technique using a computer workstation;

performing digital image processing of one or more images related to the molecular structure of the biological tissue using the computer workstation; and storing and displaying data received from the one or more characterization devices performing the one or more characterization techniques.

12. The method of claim 11, wherein the digital image processing comprises one or more of: producing a discrete two-dimensional Fourier transform of the one or more images, performing image segmentation of the one or more images, defining descriptors of boundaries or regions in the one or more images, and recognizing objects in the one or more images.

13. The method of claim 7, wherein the X-ray diffraction uses an X-ray tissue diffractometer comprising:

a positioning area for the biological tissue;

an X-ray beam delivery system providing a primary incident micro-beam of X-rays directed at the biological tissue to be analyzed, wherein the X-ray beam delivery system comprises:

a radiation source operating in a continuous mode;

an apparatus forming the primary incident micro-beam of X-rays;

a monochromator; and at least one of a collimating optical device and a focusing optical device; and a receiver comprising a two-dimensional pixel detector designed to detect a transmitted micro-beam of X-rays passed through the biological tissue as well as part or all of X-rays that are diffracted by the biological tissue.

14. The method of claim 13, wherein the two-dimensional pixel detector is inside a protection container, wherein the protection container comprises a vacuum or an inert gas environment, and a window or wall facing the biological tissue that is substantially transparent to the X-rays.

15. The method of claim 14, wherein the inert gas environment comprises neon or helium.

16. The method of claim 13, wherein the X-ray tissue diffractometer further comprises a chamber filled with an inert gas wherein the chamber is located between the two-dimensional pixel detector and the biological tissue during an X-ray diffraction characterization of the molecular structure of the biological tissue.

17. The method of claim 16, wherein the inert gas is neon or helium.

18. The method of claim 1, wherein the target disease in the animal comprises diseases of the immune system, rheumatic diseases, cancer, or diseases of one or more of the: skin, stomach, liver, rectum, colon, esophagus, pancreas, bladder, vagina, lung, oropharynx, nasopharynx, oral mucosa, tongue, brain, thyroid, prostate, breast, cervix, ovary, urological organs, endocrine organs, veins, lymph nodes, mammary glands, respiratory organs, digestive organs, heart, blood vessels, colon, ear, throat, or nose.

19. The method of claim 1, further comprising monitoring a clinical response of the animal comprising one or more of: a general blood test, a biochemical analysis, and a urine analysis, and using information from the monitoring to further determine the efficacy of the therapeutic agent.

20. The method of claim 1, further comprising developing a dose-response curve for the therapeutic agent, using the observed changes of the molecular structure of the biological tissue.

21. The method of claim 1, further comprising developing a dose and dosing interval for the therapeutic agent using the observed changes of the molecular structure of the biological tissue.

22. The method of claim 1, further comprising measuring the molecular structure of the biological tissue at a plurality of times using the non-invasive biological tissue characterization technique, wherein the plurality of times comprises the first time and the second time.

23. The method of claim 22, wherein the observing the change of the molecular structure of the biological tissue further comprises comparing regression coefficients of functions fit to data from the measurements of the molecular structure of the biological tissue at the plurality of times.

24. The method of claim 1, wherein the animal is selected from rabbits, guinea pigs, white rats, white mice, golden hamsters, and monkeys.

25. The method of claim 1, further comprising determining a median effective dose (ED50) of the therapeutic agent using the non-invasive biological tissue characterization technique.

26. The method of claim 25, further comprising calculating a therapeutic index (TI) from the ED50 and a median lethal dose (LD50), wherein the TI is the LD50 divided by the ED50.

27. The method of claim 1, further comprising monitoring a clinical response of the animal selected from one or more of: a blood test, a biochemical analysis, and a urine analysis.

* * * * *